(12) United States Patent
Cheng et al.

(10) Patent No.: US 9,901,242 B2
(45) Date of Patent: Feb. 27, 2018

(54) HOST, OPTICAL LENS MODULE AND DIGITAL DIAGNOSTIC SYSTEM INCLUDING THE SAME

(75) Inventors: Chu-Ming Cheng, Hsinchu (TW); Long-Sheng Liao, Hsinchu (TW); Yu-Tsung Lee, Hsinchu (TW)

(73) Assignee: Medimaging Integrated Solution, Inc., Hsinchu (TW)

( * ) Notice: Subject to any disclaimer, the term of this patent is extended or adjusted under 35 U.S.C. 154(b) by 54 days.

(21) Appl. No.: 13/338,813

(22) Filed: Dec. 28, 2011

(65) Prior Publication Data
US 2013/0083183 A1     Apr. 4, 2013

(30) Foreign Application Priority Data

Oct. 4, 2011   (TW) .............................. 100135866 A

(51) Int. Cl.
| | |
|---|---|
| *A61B 1/00* | (2006.01) |
| *A61B 1/227* | (2006.01) |
| *A61B 1/233* | (2006.01) |
| *A61B 1/267* | (2006.01) |
| *A61B 3/12* | (2006.01) |
| *A61B 5/00* | (2006.01) |

(52) U.S. Cl.
CPC ...... *A61B 1/00108* (2013.01); *A61B 1/00034* (2013.01); *A61B 1/00105* (2013.01); *A61B 1/00188* (2013.01); *A61B 1/227* (2013.01); *A61B 1/233* (2013.01); *A61B 1/267* (2013.01); *A61B 3/1208* (2013.01); *A61B 5/0077* (2013.01); *A61B 2560/0406* (2013.01); *A61B 2560/0443* (2013.01)

(58) Field of Classification Search
CPC .......... H04N 2005/2255; A61B 1/0019; A61B 1/04; A61B 1/06; A61B 1/07; A61B 1/00163; A61B 1/00112; A61B 1/00002; A61B 1/00034; A61B 1/00105; A61B 1/00108; A61B 1/00188; A61B 1/227; A61B 2560/0406; A61B 2560/0443; A61B 3/1208; A61B 5/0077
USPC .... 348/65–66, 68, 73, 75–77; 600/109, 130, 600/199–200; 695/65–66, 68, 73, 75–77
See application file for complete search history.

(56) References Cited

U.S. PATENT DOCUMENTS

| | | | | |
|---|---|---|---|---|
| 6,069,651 | A * | 5/2000 | Tsuyuki et al. | 348/75 |
| 6,361,489 | B1 * | 3/2002 | Tsai | 600/109 |
| 6,957,907 | B2 * | 10/2005 | Fischer et al. | 362/573 |
| 7,419,467 | B2 * | 9/2008 | Tsai | A61B 1/00052 600/109 |
| 7,691,056 | B2 * | 4/2010 | Hirata | 600/129 |
| 2002/0038076 | A1 * | 3/2002 | Sheehan et al. | 600/200 |

(Continued)

*Primary Examiner* — Gelek W Topgyal
(74) *Attorney, Agent, or Firm* — Muncy, Geissler, Olds & Lowe, P.C.

(57) ABSTRACT

A digital diagnostic system with interchangeable lenses includes a host and at least one optical lens module, wherein the host without any optical lens having curved surface includes a focus adjustment module which drives an image capture module to linearly move. Therefore, the optical system of the optical lens module can be designed independently, and no need to include focus adjustment mechanism, so that the optical design of the optical lens module can be greatly simplified, and the system allows a greater mechanism tolerance, thereby reducing manufacturing difficulty and manufacturing cost.

26 Claims, 5 Drawing Sheets

(56) References Cited

U.S. PATENT DOCUMENTS

| | | | |
|---|---|---|---|
| 2002/0085272 A1* | 7/2002 | Tomioka et al. | 359/362 |
| 2005/0182291 A1* | 8/2005 | Hirata | 600/101 |
| 2006/0140470 A1* | 6/2006 | Watanabe | 382/142 |
| 2006/0200001 A1* | 9/2006 | Keller | 600/160 |
| 2007/0229701 A1* | 10/2007 | Aiba | 348/373 |
| 2008/0204581 A1* | 8/2008 | Tsugita | G09G 3/2003 348/273 |
| 2008/0225299 A1* | 9/2008 | Ono | 356/447 |
| 2011/0157457 A1* | 6/2011 | Mo | H04N 5/23212 348/349 |

* cited by examiner

HOST, OPTICAL LENS MODULE AND DIGITAL DIAGNOSTIC SYSTEM INCLUDING THE SAME

BACKGROUND OF THE INVENTION

1. Field of the Invention

The present invention relates to a digital diagnostic system, and more particularly to a host with interchangeable optical lenses, an optical lens module, and a digital diagnostic system including the same.

2. Description of the Prior Art

A digital diagnostic system of prior art is composed of a host and a lens which are combined into one body. Therefore, it's necessary that a doctor uses a corresponding digital diagnostic system to observe different affected parts, such as ophthalmic fundus, ear canal, or skin etc., which results in that whole costs can not be reduced.

Another digital diagnostic system of prior art is designed to be a host with detachable lenses so that a doctor may use one host to observe various affected parts of a patient with different kinds of lenses. However, in the digital diagnostic system of prior art, optical lenses with curved surfaces and coupled with each other are respectively arranged at the host end and the lens end. To couple various lenses for different purposes with the host, the optical design of the system is more complicated. Alternatively, it increases manufacturing difficulty for arranging a focus adjustment mechanism with higher precision, such as a cam ring, at the lens end.

Accordingly, it is highly desirable to simplify the optical design of a digital diagnostic system, which makes single host to be coupled with various lenses for different purposes and provides an image with better image quality.

SUMMARY OF THE INVENTION

The present invention proposes a host, an optical lens module, and a digital diagnostic system including the same, wherein the host without an optical lens with a curved surface simplifies the optical design of the lens end. In addition, the host end includes a focus adjustment module for driving an image capture module, which compensates the differences of focal length between various optical lens modules. Therefore, the optical design of the lens end can be simplified, and the system allows a greater mechanism tolerance to reduce manufacturing difficulty and manufacturing cost.

In one embodiment of the present invention, the proposed digital diagnostic system comprises a host and at least one optical lens module. The host includes an image capture module, a display module, a processing unit, a focus adjustment module, an adapter, and a power module. The image capture module is used for capturing a reflected light from an affected part to form an image. The display module is used for displaying the image captured by the image capture module. The processing unit is electrically connected to the image capture module and the display module, and the processing unit is used for processing the image and displaying the image on the display module. The focus adjustment module is used for driving the image capture module to physically and linearly move along an image capturing direction. The adapter is arranged in front of the image capture module. The power module supplies power to the digital diagnostic system in operation. The image capture module, the display module, the processing unit, the focus adjustment module and the power module are arranged in an interior of the host. The optical lens module is detachably connected to the adapter for interchanging another optical lens module to capture the image of another affected part. The optical lens module comprises a plurality of optical lenses and a light source. The optical lenses have a plurality of curved surfaces for converging the reflected light on the image capture module, wherein a distance from the optical lenses to the adapter is fixed during focusing. The light source is positioned off an optical axis of the optical lens for providing illumination light to illuminate the affected part.

In another embodiment of the present invention, the proposed host composes a digital diagnostic system with at least one optical lens module. The host comprises an image capture module, a display module, a processing unit, a focus adjustment module, an adapter, and a power module. The image capture module is used for capturing a reflected light from an affected part to form an image. The display module is used for displaying the image captured by the image capture module. The processing unit is electrically connected to the image capture module and the display module, and the processing unit is used for processing the image and displaying the image on the display module. The focus adjustment module is used for driving the image capture module to physically and linearly move along an image capturing direction. The adapter is arranged in front of the image capture module for connecting the optical lens module so that the optical lens module can converge the reflected light on the image capture module. The power module supplies power to the digital diagnostic system in operation. The image capture module, the display module, the processing unit, the focus adjustment module and the power module are arranged in an interior of the host.

In yet another embodiment of the present invention, the proposed optical lens module composes the digital diagnostic system with a host without an optical lens with a curved surface, wherein the host comprises an adapter and an image capture module physically and linearly moving along an image capturing direction. The optical lens module is detachably connected to the adapter of the host for interchanging another optical lens module and comprises a plurality of optical lenses and a light source. The optical lenses have a plurality of curved surfaces for converging a reflected light from an affected part on the image capture module of the host to form an image, wherein a distance from the optical lenses to the adapter is fixed during focusing. The light source is positioned off an optical axis of the optical lens for providing illumination light to illuminate the affected part.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENT

The detailed explanation of the present invention is described as follows. The described preferred embodiments are presented for purposes of illustrations and description, and they are not intended to limit the scope of the present invention.

Figure 1:
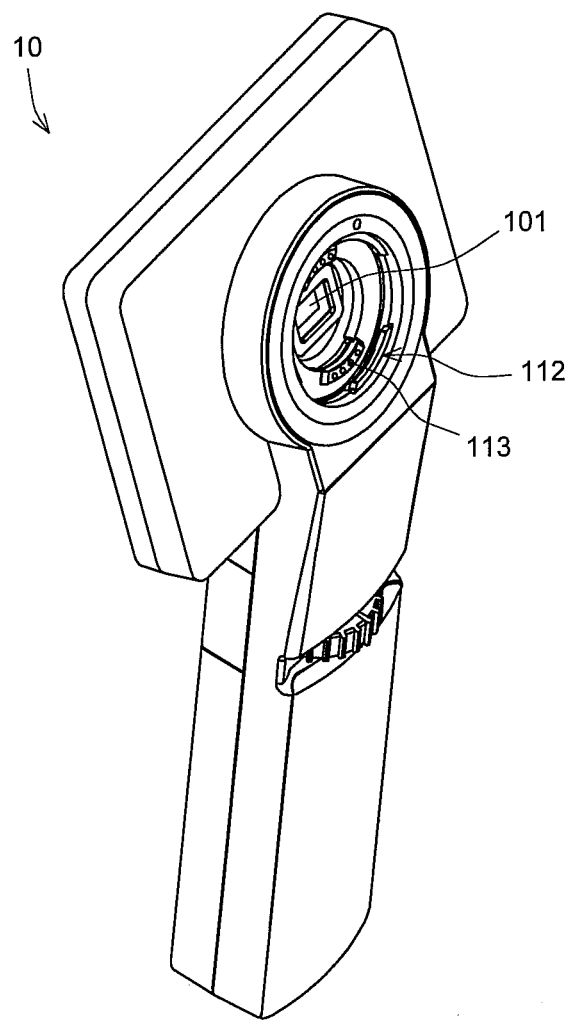
FIG. 1 is a diagram schematically illustrating a host of a digital diagnostic system according to an embodiment of the present invention.
Figure 2A:
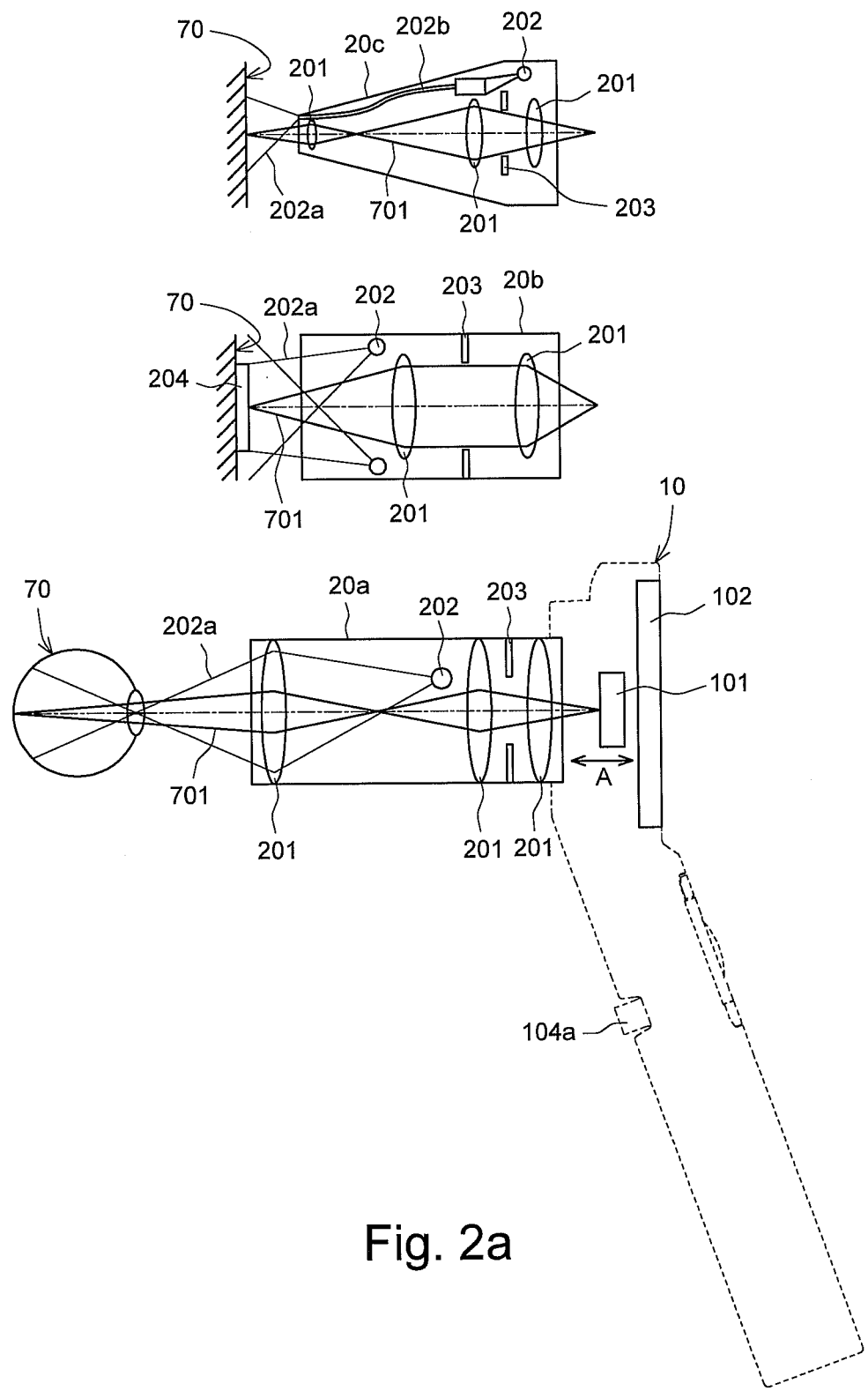
FIG. 2a and FIG. 2b are diagrams schematically illustrating a plurality of optical lens modules of a digital diagnostic system according to an embodiment of the present invention.
Figure 2B:
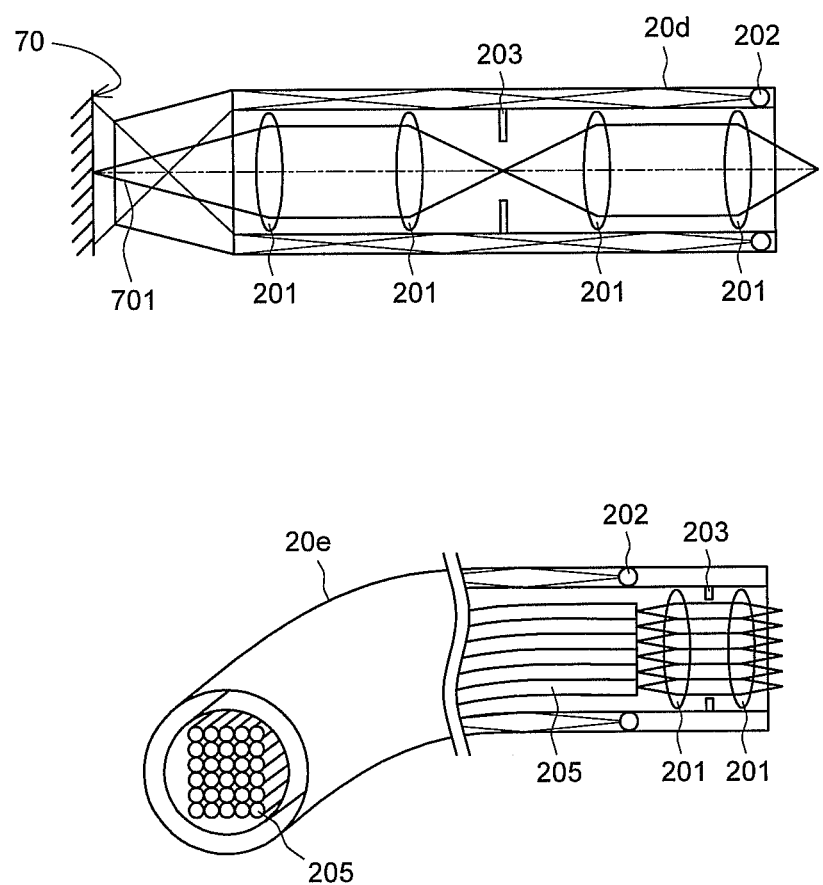
Figure 3:
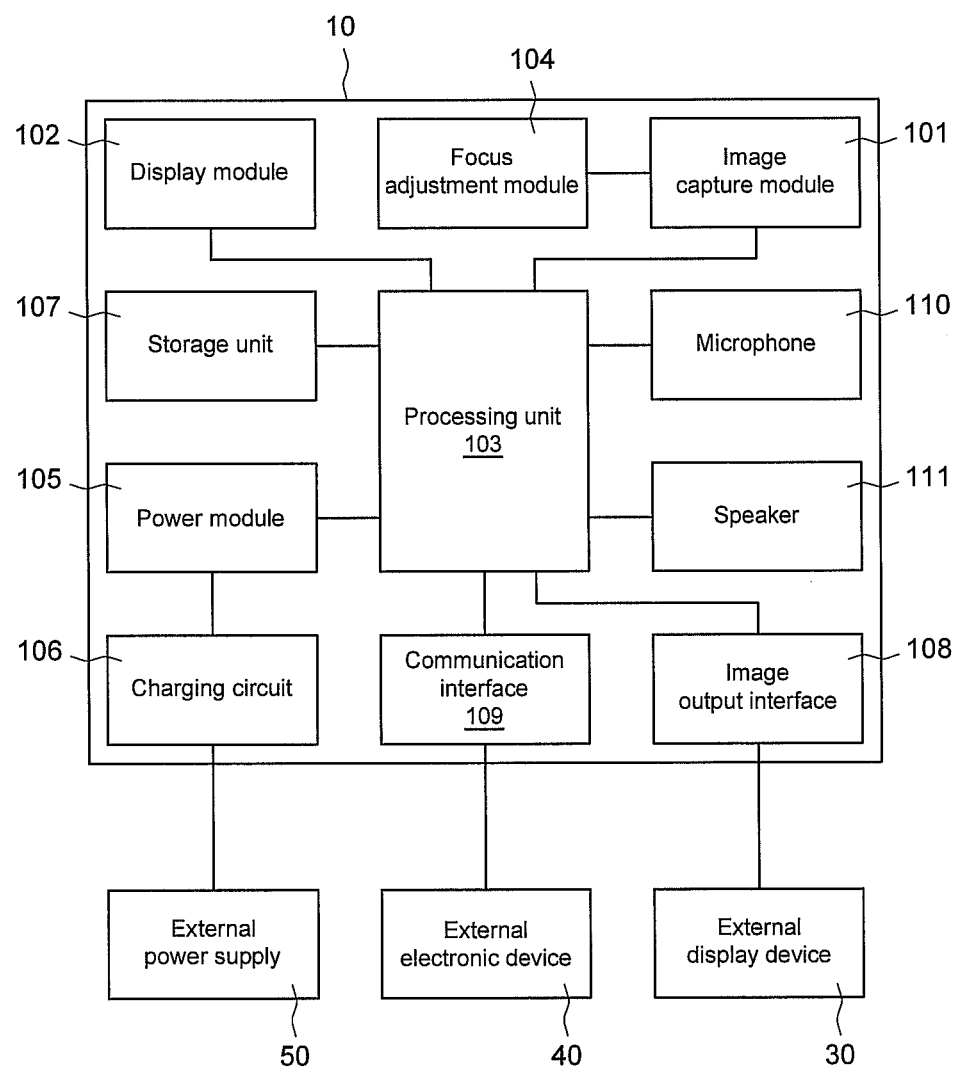
FIG. 3 is a block diagram illustrating a host of a digital diagnostic system according to an embodiment of the present invention.

Referring to FIGS. 1, 2 and 3, an embodiment of a digital diagnostic system according to the present invention comprises a host (10) and at least one optical lens module (20a, 20b, 20c, 20d and 20e). The host (10) comprises an image capture module (101), a display module (102), a processing unit (103), a focus adjustment module (104), an adapter (112), and a power module (105). The image capture module (101) is used for capturing a reflected light (701) from an affected part (70) to form an image. The display module (102) is used for displaying the image captured by the image capture module (101). The processing unit (103) is electrically connected to the image capture module (101) and the display module (102). The processing unit (103) is used for processing the image captured by the image capture module (101) and displaying the image on the display module (102). For example, the processing unit (103) processes the image captured by the image capture module (101) such as eliminating noise, adjusting contrast, or adjusting brightness, to get better image quality.

The focus adjustment module (104) is used for driving the image capture module (101) to physically and linearly move along an image capturing direction presented by an arrow A shown in FIG. 2a. For example, to find the appropriate focal length, a user may utilize an exposed adjusting ring (104a) on exterior part of the host (10) to drive the image capture module (101) to move backwards and forwards along the direction of arrow A. It is noted that the focus adjustment module (104) can be driven by manual and electrical operation. The adapter (112) is arranged in front of the image capture module (101) so that the optical lens module (20a, 20b, 20c, 20d or 20e) can be detachably connected to the adapter (112). For example, the optical lens module (20a, 20b, 20c, 20d or 20e) may be clamped with or screw on the adapter (112). The optical lens module (20a, 20b, 20c, 20d or 20e) connected to the adapter (112) is coupled to the image capture module (101) so that the reflected light (701) of the affected part (70) is converged on the image capture module (101) to form the image. The power module (105) is used for supplying power to the digital diagnostic system in operation. The power module (105) may be a primary or rechargeable battery. In one embodiment of the present invention, the host (10) comprises a charging circuit (106) which is electrically connected to the power module (105). When the host (10) is electrically connected to an external power supply (50), the charging circuit (106) can utilize the external power supply (50) for charging the power module (105).

Referring to FIG. 2a and FIG. 2b, in one embodiment of the present invention, the optical lens module (20a, 20b, 20c, 20d or 20e) comprises a plurality of optical lenses (201) and a light source (202). A lens set including the plurality of lenses (201) has a plurality of curved faces so that the reflected light (701) of the affected part (70) can converge on the image capture module (101). The light source (202) is positioned off an optical axis of the optical lens (201). The light source (202) provides an illumination light (202a) for illuminating the affected part (70). In a preferred embodiment of the present invention, the optical lens module (20a, 20b, 20c, 20d or 20e) further comprises a diaphragm (203) arranged between the optical lenses (201). The diaphragm (203) arranged in interior of the optical lens module (20a, 20b, 20c, 20d or 20e) can increase symmetry for reducing some odd-order aberrations of an image and enhancing image quality.

It is noted that, by appropriate design, different kinds of optical lens modules (20a, 20b, 20c, 20d, 20e) can be used for inspecting various affected part (70). For example, the light source (202) can be specially designed to emit the illumination light (202a) onto fundus oculi of an eye effectively. Alternatively, a contact plate (204) with a specific refraction rate can be arranged on the optical lens module (20b) shown in FIG. 2a to make greater part of the illumination light (202a) emit into an inner layer of skin so that the ratio of the illumination light (202a) reflected by the skin can be reduced. Furthermore, in order to provide illumination for the inside of a long and narrow channel, such as a ear canal, the optical lens module (20c) shown in FIG. 2a may utilize an optical element such as a collimator to guide the illumination light (202a) emitted from the light source (202) into an optical fiber (202b), and thereby the illumination light (202a) is emitted from the other end of the optical fiber (202b) to the inside of the long and narrow channel. It is noted that the optical lens module is not limited to these embodiments described above. For example, the optical lens module may be an ophthalmoscope lens, an otoscope lens, a dermatoscope lens, a microcirculation scope lens, a rhinoscope lens (such as the optical lens module (20d) shown in FIG. 2b), a laryngoscope lens (such as the optical lens module (20e) shown in FIG. 2b), or an endoscopy lens, etc. Be additionally noted, the light source (202) of the optical lens module (20d, 20e) shown in FIG. 2b, the illumination light (202a) is suitably guided to the affected part (70) by appropriate design. For example, the illumination light (202a) emitted from the light source (202) may be reflected within an optical fiber or an inner wall of a tube to the affected part (70). Alternatively, it may utilize an optical fiber (205) to collect the reflected light from the affected part to the image capture module as presented by the optical lens module (20e) shown in FIG. 2b.

In one embodiment of the present invention, the host (10) comprises a plurality of first conductive contacts (113), and the optical lens module (20a, 20b, 20c, 20d or 20e) comprises a plurality of second conductive contacts (not shown). When the optical lens module (20a, 20b, 20c, 20d or 20e) is connected to the adapter (112) of the host (10), the plurality of second conductive contacts of the optical lens module are electrically connected to the corresponding first conductive contacts (113) of the host (10) so that the light source (202) of the optical lens module can be electrically connected to the power module (105) of the host (10), thus the power is acquired for emitting a illumination light. In one embodiment of the present invention, the processing unit (103) determines a type of the optical lens module connected to the adapter (112) according to a connected configuration of the first conductive contacts (113). For example, if there are four first conductive contacts (113), one of them is grounding and the other three first conductive contacts (113) are arranged as a vector to obtain a combination of 2×2×2. The optical lens module has seven configurations for identification except that optical lens module is not connected. In a preferred embodiment of the present invention, the processing unit (103) can further set the mode of the image capture module (101) and adjust the internal setting value to obtain better image quality.

According to the above-mentioned structure, the interior of the host (10) does not have any optical lens, i.e. it does not include any optical lens with curved surfaces. Therefore, an external optical lens module is independently designed to be maximized and optimized. In one embodiment of the present invention, the host (10) comprises a cover plate (not shown) arranged between the image capture module (101) and the adapter (112), which is for protecting the image capture module (101). In addition, the focus adjustment module (104) is independently arranged in interior of the host (10) for driving the image capture module (101) to physically and linearly move, that means the back focus of the optical lens module can be capable of optionally adjusting. Therefore, the optical lens module does not need any other mechanism for adjusting focal length, particularly a designed cam ring for nonlinear compensation, so that the optical design of the optical lens module can be further simplified, and the system allows a greater mechanism tolerance to reduce manufacturing difficulty and manufacturing cost.

Referring to FIG. 3, in one embodiment of the present invention, the host (10) further comprises a storage unit (107) which is electrically connected to the processing unit (103). The storage unit (107) is used for storing images captured by the image capture module (101) so that a doctor's human errors in sketching an affected part on a paper can be reduced. The storage unit (107) may be a flash memory, a hard disk, or a combination thereof. For example, the storage unit (107) may be a memory card.

In one embodiment of the present invention, the host (10) further comprises an image output interface (108) which is electrically connected to the processing unit (103). The image output interface (108) is used for connecting an external display device (30) to the digital diagnostic system of the present invention therethrough so that patients under treatment can synchronously observe the image of the affected part.

In one embodiment of the present invention, the host (10) further comprises a communication interface (109) which is electrically connected to the processing unit (103). The communication interface (109) is used for connecting an external electronic device (40) to the digital diagnostic system of the present invention therethrough. Hence, diagnostic data stored in the digital diagnostic system of the present invention can be transmitted to the external electronic device (40) via the communication interface (109). For example, the communication interface (109) may be universal serial bus (USB) interface; and the external electronic device (40) may be a computer.

In one embodiment of the present invention, the host (10) further comprises a microphone (110) electrically connected to the processing unit (103). The microphone (110) is used for receiving a voice from a user (such as a doctor) and converting the voice into an audio signal. The audio signal acquired by the microphone (110) can be stored in the storage unit (107) to record the voice from the user so that it provides convenience for data trace and analysis. In a preferred embodiment of the present invention, the host (10) further comprises a speaker (111) electrically connected to the processing unit (103). The speaker (111) is used for outputting the audio signal acquired by the microphone (110) to avoid inconvenience of transmitting audio signal or connecting an external speaker.

Figure 4:
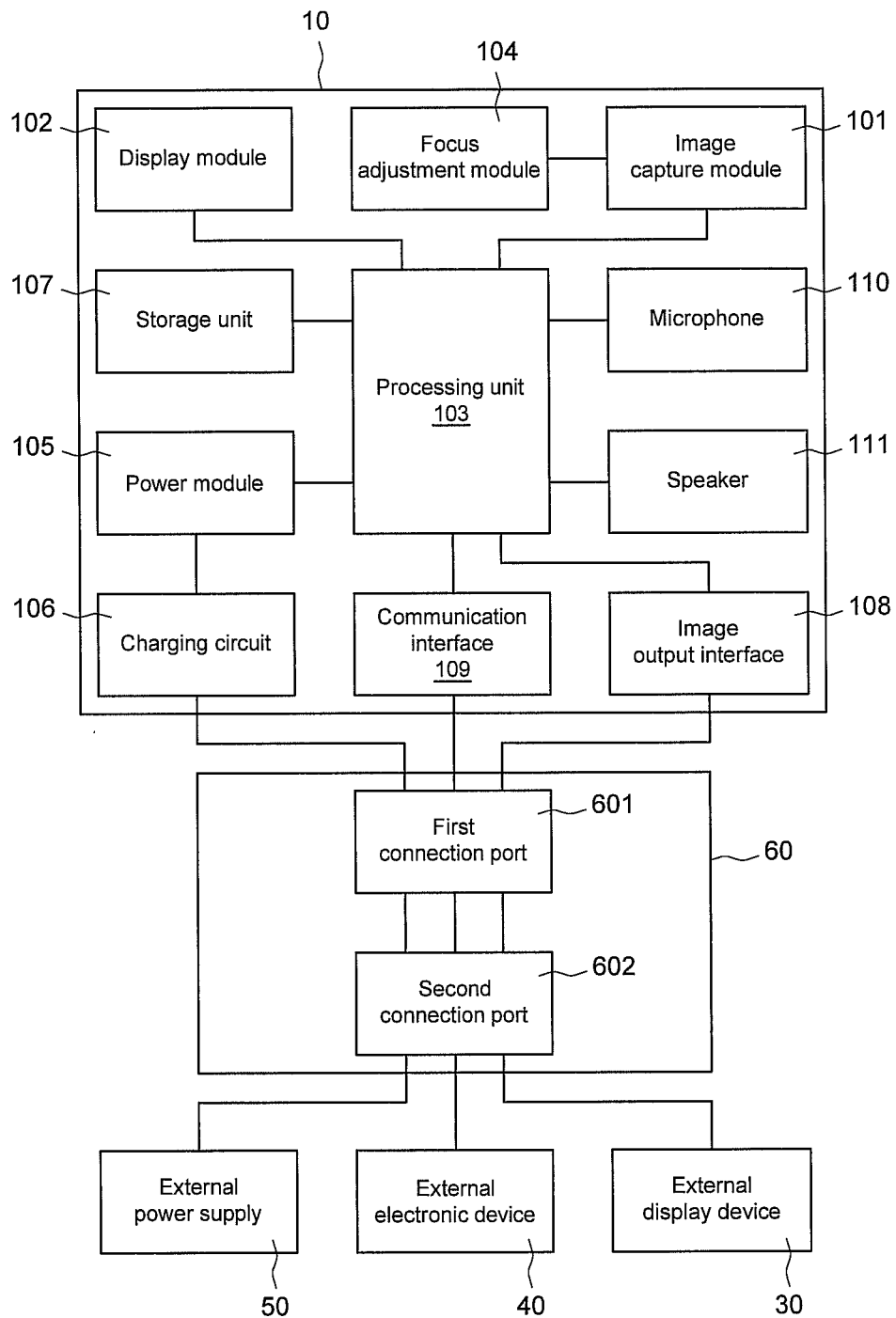
FIG. 4 is a block diagram illustrating a host and a base of a digital diagnostic system according to an embodiment of the present invention.

Referring to FIG. 4, in one embodiment, the proposed digital diagnostic system comprises a base (60) having a first connection port (601) and a second connection port (602). The first connection port (601) is used for electrically connecting, respectively or simultaneously, to at least one of the image output interface (108), the communication interface (109), and the charging circuit (106) of the host (10). The second connection port (602) is used for electrically connecting to at least one of the external display device (30), the external electronic device (40), and the external power supply (50). Therefore, the host (10) can be electrically connected to the external display device (30), the external electronic device (40), or the external power supply (50) via the base (60). It is noted, in the embodiment shown in FIG. 3 and FIG. 4, the charging circuit (106) is arranged in the host (10), but not limited to the embodiment, the charging circuit (106) may be also arranged in the base (60).

In conclusion, the host end of the digital diagnostic system according to the present invention does not have any optical lens with curved surface so that the optical design of the lens end can be greatly simplified. In addition, the host includes the focus adjustment module driving the image capture module to linearly move to compensate differences of focal length between various optical lens modules, and hence it's not necessary to arrange a focus adjustment mechanism in the lens end. Therefore, the optical design of the optical lens module can be further simplified, and the system allows a greater mechanism tolerance to reduce manufacturing difficulty and manufacturing cost.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the spirit and scope of the appended claims.

What is claimed is:

1. A digital diagnostic system, comprising:
a host without an optical lens with a curved surface, the host comprises:
an image capture module, for capturing a reflected light from an affected part to form an image;
a display module, for displaying the image captured by the image capture module;
a processing unit electrically connected to the image capture module and the display module, for processing the image and displaying the image on the display module;
a focus adjustment module, for driving the image capture module to physically and linearly move along an image capturing direction;
an adapter arranged in front of the image capture module;
a power module, for supplying power to the digital diagnostic system in operation, wherein the image capture module, the display module, the processing unit, the focus adjustment module and the power module are arranged in an interior of the host; and
a plurality of first conductive contacts; and
at least one optical lens module detachably connected to the adapter for interchanging another optical lens module to capture the image of another affected part, wherein the optical lens module comprises:
a plurality of optical lenses being respectively disposed at fixed positions and having a plurality of curved surfaces, for converging the reflected light on the image capture module, wherein a distance from the optical lenses to the adapter is fixed while the focus adjustment module is utilized for only driving the image capture module to physically and linearly move along an image capturing direction to find the appropriate focal length;

a light source positioned off an optical axis of the optical lens, for providing illumination light to illuminate the affected part; and a plurality of second conductive contacts electrically connected to the light source and the corresponding first conductive contacts to allow the power to be supplied from the power module of the host to the light source and the processing unit to determine a type of the optical lens module according to a connected configuration of the first conductive contacts when the optical lens module is connected to the adapter; and set a mode of the image capture module and adjust an internal setting value to obtain better image quality.

2. The digital diagnostic system according to claim 1, wherein the optical lens module further comprises an optical fiber, for collecting the reflected light to the image capture module.

3. The digital diagnostic system according to claim 1, wherein the optical lens module further comprises a diaphragm arranged between the optical lenses.

4. The digital diagnostic system according to claim 1, wherein the optical lens module comprises an ophthalmoscope lens, an otoscope lens, a dermatoscope lens, a microcirculation scope lens, a rhinoscope lens, a laryngoscope lens or an endoscopy lens.

5. The digital diagnostic system according to claim 1, wherein the host further comprises a storage unit electrically connected to the processing unit, for storing the image captured by the image capture module.

6. The digital diagnostic system according to claim 5, wherein the storage unit comprises a flash memory, a hard disk, or a combination thereof.

7. The digital diagnostic system according to claim 1, wherein the host further comprises an image output interface electrically connected to the processing unit, for connecting an external display device to the digital diagnostic system therethrough.

8. The digital diagnostic system according to claim 1, wherein the host further comprises a communication interface electrically connected to the processing unit, for connecting an external electronic device to the digital diagnostic system therethrough.

9. The digital diagnostic system according to claim 1, wherein the host further comprises a microphone electrically connected to the processing unit, for receiving a voice from a user and converting the voice into an audio signal.

10. The digital diagnostic system according to claim 9, wherein the host further comprises a speaker electrically connected to the processing unit, for outputting the audio signal.

11. The digital diagnostic system according to claim 1, wherein the host further comprises a cover plate arranged between the image capture module and the adapter, for protecting the image capture module.

12. The digital diagnostic system according to claim 1, comprising a charging circuit electrically connected to the power module, for charging the power module with an external power supply.

13. The digital diagnostic system according to claim 1, further comprising:

a base comprising a first connection port and a second connection port; wherein the first connection port is used for electrically connecting to at least one of an image output interface, an communication interface, and a charging circuit of the digital diagnostic system; and the second connection port is used for electrically connecting to at least one of an external display device, an external electronic device, and an external power supply.

14. A host without an optical lens with a curved surface, for composing a digital diagnostic system with at least one optical lens module with a light source, a plurality of second conductive contacts and a plurality of optical lenses being respectively disposed at fixed positions and having a plurality of curved surfaces, comprising:

an image capture module, for capturing a reflected light from an affected part to form an image;

a display module, for displaying the image captured by the image capture module, a processing unit electrically connected to the image capture module and the display module, for processing the image and displaying the image on the display module;

a focus adjustment module, for driving the image capture module to physically and linearly move along an image capturing direction;

an adapter arranged in front of the image capture module, for connecting the optical lens module to converge the reflected light on the image capture module, wherein a distance from the optical lenses to the adapter is fixed while the focus adjustment module is utilized for only driving the image capture module to physically and linearly move along an image capturing direction to find the appropriate focal length;

a power module, for supplying power to the digital diagnostic system in operation, wherein the image capture module, the display module, the processing unit, the focus adjustment module and the power module are arranged in an interior of the host; and a plurality of first conductive contacts electrically connected to the corresponding second conductive contacts to allow the power to be supplied from the power module of the host to the light source and the processing unit to determine a type of the optical lens module according to a connected configuration of the first conductive contacts when the optical lens module is connected to the adapter; and set a mode of the image capture module and adjust an internal setting value to obtain better image quality.

15. The host according to claim 14, further comprising:

a storage unit electrically connected to the processing unit, for storing the image captured by the image capture module.

16. The host according to claim 15, wherein the storage unit comprises a flash memory, a hard disk, or a combination thereof.

17. The host according to claim 14, further comprising:

an image output interface electrically connected to the processing unit, for connecting an external display device to the digital diagnostic system therethrough.

18. The host according to claim 14, further comprising:

a communication interface electrically connected to the processing unit, for connecting an external electronic device to the digital diagnostic system therethrough.

19. The host according to claim 14, further comprising:
a microphone electrically connected to the processing unit, for receiving a voice from a user and converting the voice into an audio signal.

20. The host according to claim 19, further comprising:
a speaker electrically connected to the processing unit, for outputting the audio signal.

21. The host according to claim 14, further comprising:
a cover plate arranged between the image capture module and the adapter, for protecting the image capture module.

22. The host according to claim 14, further comprising:
a charging circuit electrically connected to the power module, for charging the power module with an external power supply.

23. An optical lens module for composing a digital diagnostic system with a host without an optical lens with a curved surface, wherein the host comprises an adapter, an image capture module moving physically and linearly along an image capturing direction driven by a focus adjustment module, and a plurality of first conductive contacts, and the optical lens module is detachably connected to the adapter of the host for interchanging another optical lens module, the optical lens module comprising:
a plurality of optical lenses being respectively disposed at fixed positions and having a plurality of curved surfaces, for converging a reflected light from an affected part on the image capture module of the host to form an image, wherein a distance from the optical lenses to the adapter is fixed while the focus adjustment module is utilized for only driving the image capture module to physically and linearly move along an image capturing direction to find the appropriate focal length;
a light source positioned off an optical axis of the optical lens, for providing illumination light to illuminate the affected part; and
a plurality of second conductive contacts electrically connected to the light source and the corresponding first conductive contacts to allow the power to be supplied from the power module of the host to the light source and the processing unit to determine a type of the optical lens module according to a connected configuration of the first conductive contacts when the optical lens module is connected to the adapter; and set a mode of the image capture module and adjust an internal setting value to obtain better image quality.

24. The optical lens module according to claim 23, further comprising:
an optical fiber, for collecting the reflected light to the image capture module of the host.

25. The optical lens module according to claim 23, further comprising:
a diaphragm arranged between the optical lenses.

26. The optical lens module according to claim 23, wherein the optical lens module comprises an ophthalmoscope lens, an otoscope lens, a dermatoscope lens, a microcirculation scope lens, a rhinoscope lens, a laryngoscope lens, or an endoscopy lens.

* * * * *